United States Patent
Desai

[19]

[11] Patent Number: 6,027,502
[45] Date of Patent: Feb. 22, 2000

[54] SURGICAL APPARATUS PROVIDING TOOL ACCESS AND REPLACEABLE IRRIGATION PUMP CARTRIDGE

[76] Inventor: Ashvin H. Desai, 2195 Trade Zone Blvd., San Jose, Calif. 95131

[21] Appl. No.: 09/015,299

[22] Filed: Jan. 29, 1998

[51] Int. Cl.[7] .................................................. A61B 17/39
[52] U.S. Cl. ........................... 606/41; 606/49; 604/131
[58] Field of Search .................................. 606/37–41, 45, 606/46, 48–50; 604/131, 151, 152

[56] References Cited

U.S. PATENT DOCUMENTS

| | | |
|---|---|---|
| 4,274,409 | 6/1981 | Bush . |
| 4,639,245 | 1/1987 | Pastrone et al. ...................... 604/152 |
| 4,998,527 | 3/1991 | Meyer . |
| 5,230,704 | 7/1993 | Moberg et al. . |
| 5,261,883 | 11/1993 | Hood et al. . |
| 5,322,503 | 6/1994 | Desai . |
| 5,395,312 | 3/1995 | Desai . |
| 5,490,836 | 2/1996 | Desai . |
| 5,562,703 | 10/1996 | Desai . |
| 5,643,301 | 7/1997 | Mollenauer .............................. 606/167 |
| 5,746,719 | 5/1998 | Farra et al. ............................. 604/151 |
| 5,810,809 | 9/1998 | Rydell ...................................... 606/49 |

*Primary Examiner*—Michael Peffley
*Assistant Examiner*—Roy Gibson
*Attorney, Agent, or Firm*—David H. Jaffer

[57] ABSTRACT

A surgical apparatus having an elongated probe assembly providing passage for irrigation and evacuation, as well as for inserting surgical tools such as an endoscope, RF electrodes and cutting tools. The probe assembly has a light weight handle for accurate positioning of the probe. An irrigation port is connected by way of a tube assembly to an irrigation pump having a novel, inexpensive, replaceable cartridge. An evacuation port on the probe assembly is connected to a tube assembly leading to an evacuation pump.

8 Claims, 5 Drawing Sheets

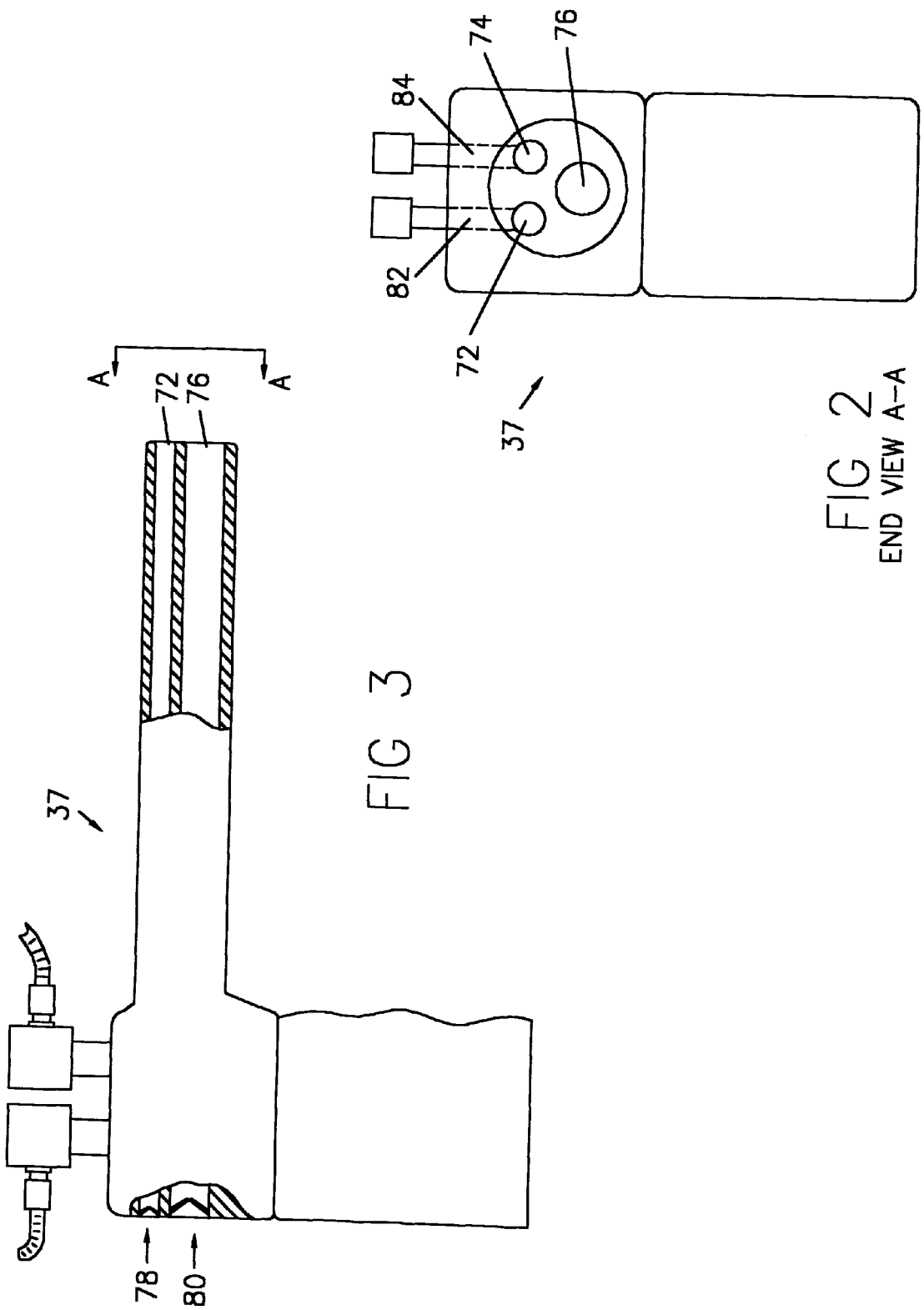

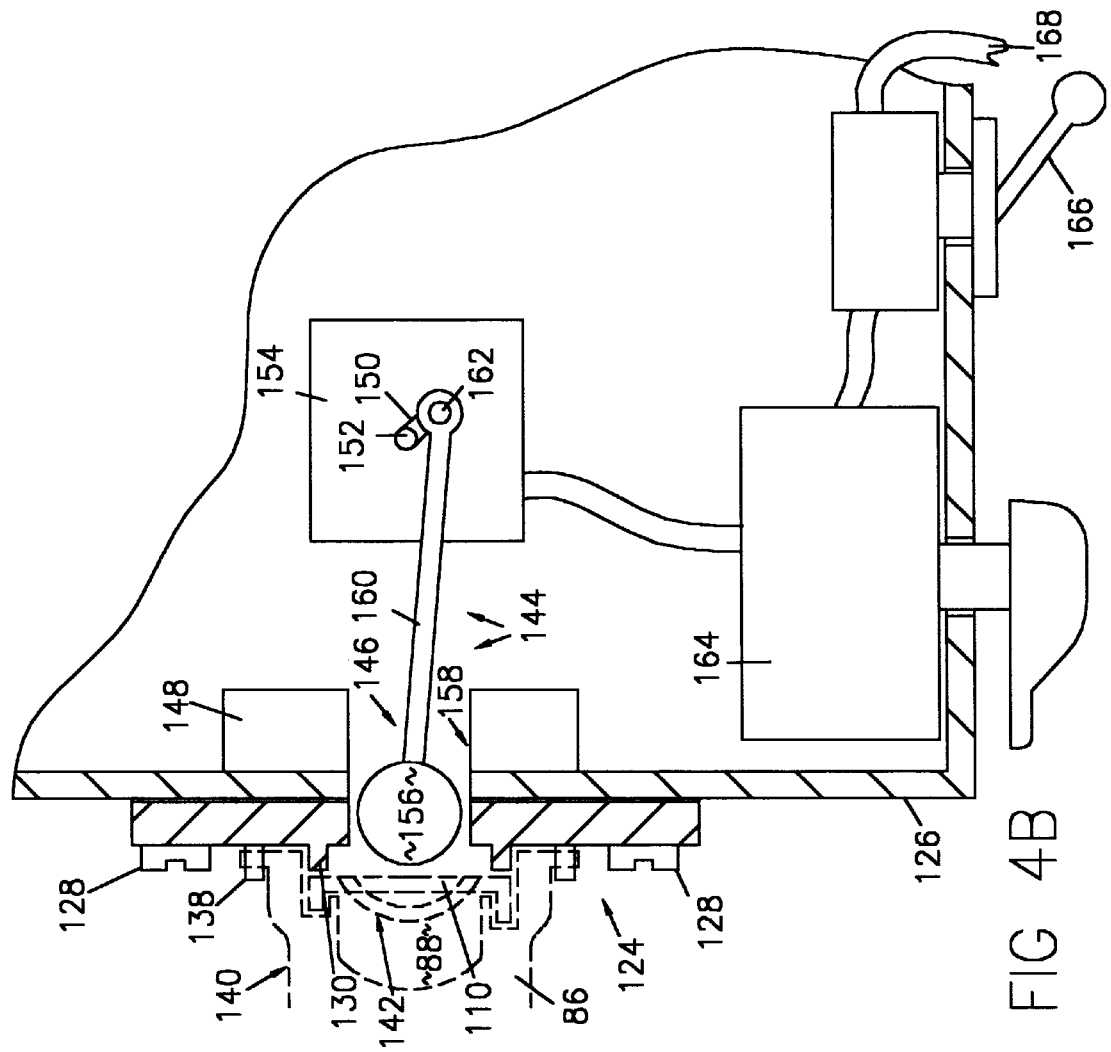
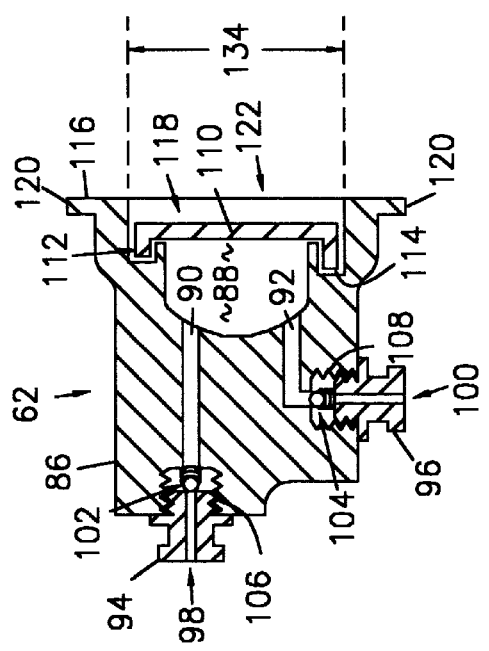
FIG 4A
FIG 4B

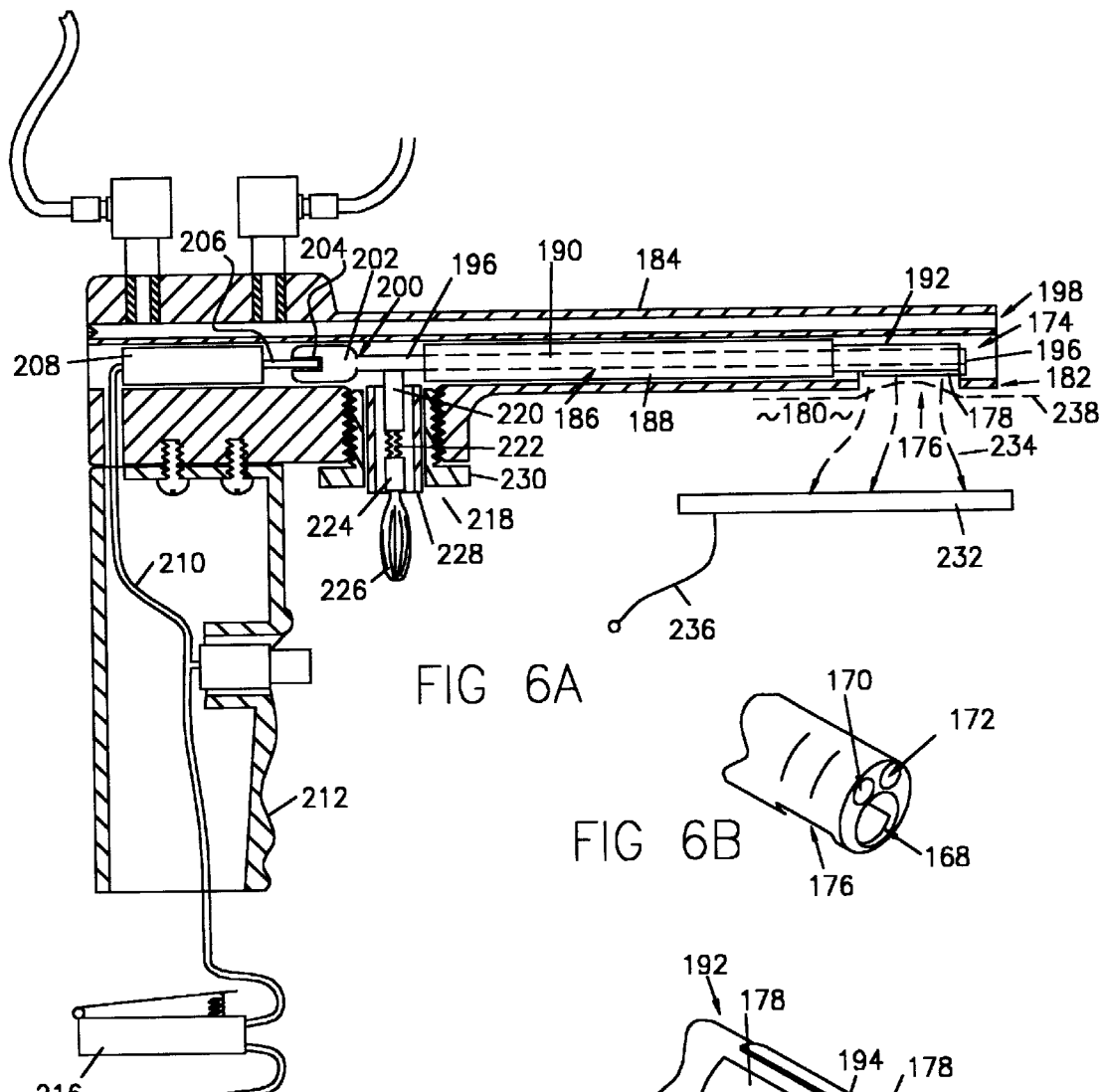

SURGICAL APPARATUS PROVIDING TOOL ACCESS AND REPLACEABLE IRRIGATION PUMP CARTRIDGE

BACKGROUND OF THE INVENTION

1. Field of the Invention

The present invention relates to surgical instrumentation and more particularly to apparatus for laparoscopic or endoscopic surgery providing tool access and a replaceable irrigation pump cartridge.

2. Brief Description of the Prior Art

Laparoscopic and endoscopic surgical instruments are used to perform surgery without the need to make large incisions, the procedure therefore being generally much less invasive than conventional surgery. Such surgical instruments include a hollow probe through which are inserted items such as an endoscope or laparoscope, a clip applier, microscissors, forceps, an optical fiber connected to a laser source for hemostatic cutting or coagulation, a set of electrodes connected to a generator for electrocautery, lines for irrigation and evacuation, etc. Multiple incisions or punctures for multiple probes are often required when more than one of the above items must be inserted at the same time. Since it is preferable to have as few punctures as possible in a patient's body, probes that can handle more than one device are desirable. It is also desirable to have as many reusable parts as possible in order to minimize costs. Reusable parts need to be designed for efficient cleaning/sterilization, and disposable parts need to be easy to replace and economical/simple in structure.

Prior art instruments have not generally been designed to meet all of the above objectives. For example, U.S. Pat. No. 5,230,704 by Moberg et al. discloses a surgical instrument designed for the singular purpose of providing suction and irrigation with hand held controls and a replaceable cartridge. A limitation of this instrument is that the location of the cartridge does not allow access for inserting additional instruments.

U.S. Pat. No. 4,274,409 by Bush describes a pump with disposable dispensing tubes (22.1, 24.1), but their installation and removal appears complex, and internal connections would need to be sterilized in order to assure proper sanitation. Bush describes the apparatus for use in a dispensing device, and not for use with an endoscopic type of instrument. Use with an endoscope/laparoscopic type of instrument does not appear to be practical.

U.S. Pat. No. 5,395,312 by Desai shows two embodiments of a surgical instrument in FIGS. 8 and 9, wherein the improvements include a disposable pump cartridge. The device of FIG. 8 shows the cartridge in the handle, and in this case sterilization of the handle bore and the motor mechanism may be required. The device of FIG. 9 avoids this problem, but in both embodiments, the cartridge blocks access to the probe, thereby restricting its use. Another disadvantage of this device is the weight in the handle due to the motor, which tends to displace the probe if not held continuously by the surgeon.

U.S. Pat. No. 5,562,703 by Desai is an example of the need to insert as many tools as possible through one probe. FIG. 17 shows a single probe through which passes an endoscope, adjustable electrodes, and irrigation fluid. This disclosure does not address the problem of a sanitary pump, or the need for a handle to control the probe position.

None of the prior art systems/devices address and solve all of the problems noted above. It is therefore clear that a more optimum instrument is needed that provides a combination of low cost, economical replacement parts, access to insert a variety of tools, and position control all in a single system.

SUMMARY OF THE INVENTION

It is therefore an object of the present invention to provide an improved tool for endoscopic/laparoscopic surgery.

It is a further object of the present invention to provide a surgical tool for endoscopic/laparoscopic surgery having a remotely located irrigation pump with an inexpensive replaceable pump cartridge.

It is a further object of the present invention to provide a surgical tool for endoscopic/laparoscopic surgery having an inexpensive replaceable pump cartridge, and facility for inserting an endoscope and other tools.

It is another object of the present invention to provide a surgical tool for endoscopic/laparoscopic surgery having an inexpensive replacement pump cartridge, facility for inserting surgical tools, and a light weight handle grip for control of the probe.

Briefly, a preferred embodiment of the present invention includes surgical apparatus having an elongated probe assembly providing passage for irrigation and evacuation, as well as for inserting surgical tools such as an endoscope, RF electrodes and cutting tools. The probe assembly has a light weight handle for accurate positioning of the probe. An irrigation port is connected by way of a tube assembly to an irrigation pump having a novel, inexpensive, replaceable cartridge. An evacuation port on the probe assembly is connected to a tube assembly leading to an evacuation pump.

An advantage of the present invention is that it provides an apparatus for endoscopic/laparoscopic surgery having an inexpensive, replaceable pump cartridge, and having access for insertion of tools through a probe assembly.

A further advantage of the present invention is that it provides an easily sterilized, reusable probe assembly, and an inexpensive, replaceable irrigation pump cartridge.

A still further advantage of the present invention is the provision of a light weight handle facilitating probe positioning without deflection due to handle weight.

IN THE DRAWING

FIG. 2 is an end view of a probe assembly showing the use of three probe bores;

FIG. 3 is a side view of the probe assembly of FIG. 2;

FIG. 4A is a cross sectional view of a novel replaceable pump cartridge;

FIG. 4B shows details of the motor drive unit of the pump assembly;

FIG. 6A shows a probe assembly having a rotatable electro-surgical apparatus;

FIG. 6B is a perspective view clarifying the arrangement of multiple bores; and

FIG. 6C is a perspective view showing multiple conductive plates.

DESCRIPTION OF THE PREFERRED EMBODIMENT

Figure 1:
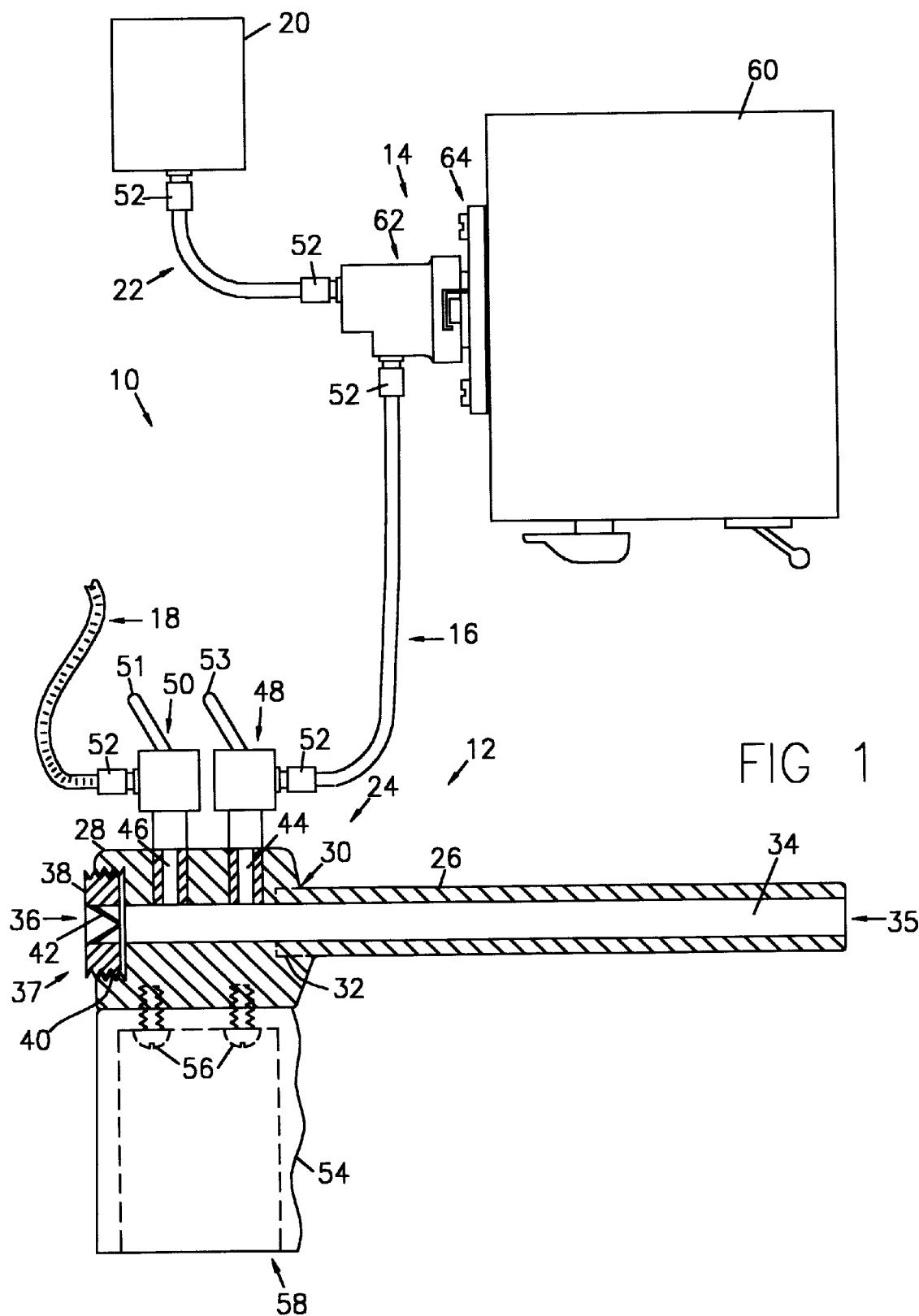
FIG. 1 illustrates a probe assembly and pump assembly of the present invention with a single bore in the probe.

Referring now to FIG. 1 of the drawing there is shown a preferred embodiment of the surgical apparatus 10 of the present invention including a probe assembly 12, and an irrigation pump assembly 14 interconnected by a tubing assembly 16. An evacuation tube assembly 18 is for connection to an evacuation pump (not shown). Irrigation fluid is provided by supply 20, connected to the irrigation pump assembly 14 through supply tube assembly 22.

The probe assembly 12 includes a probe module 24 having a probe 26 and a probe module housing 28 joined together at 30 either as an integral unit or by any of various other methods indicated by dashed line 32. If the housing 28 and probe 26 are separate parts, the method of joining can be either permanent, such as a welded, glued or soldered joint, or it can be temporary, such as with sealed threads or a connector engagement. Such methods of joining parts are understood by those skilled in the art and additional description is therefore not given. In the case of a connector or threaded joint, sealing could be done for example, with an 0-ring.

The housing 28 and probe 26 have a bore 34 therethrough, with an open distal end 35, and a proximal end 37 closed by sealed port 36, provided for insertion of tools into the bore 34. The particular design of port 36 will depend on the tool or tools to be inserted. As shown, port 36 is a threaded ring 38 engaged with a corresponding tap 40 in housing 28. The center of the ring 38 contains a flexible bicuspid value 42 which resists fluid flow outward from the bore 34, but allows sealed passage of tools. The housing 28 has an irrigation port 44 and an evacuation port 46, for providing irrigation fluids to, and evacuating material from bore 34. The irrigation port 44 receives fluid through an irrigation connector assembly 48, supplied by tube assembly 16 from the supply 20, driven by pump assembly 14. Evacuation of fluids and other material from bore 34 is through port 46 and connector 50, through tube assembly 18 to an evacuation pump (not shown). Connector assemblies 48 and 50, in addition to providing interconnection, can also provide valve control, for example as indicated by valve handles 51 and 53. Various valve and connection designs are known by those skilled in the art, and are included in the spirit of the present invention. The location of the ports 44, 46 is given as a preferred embodiment. Other configurations of the housing 28 and location and configuration of the ports 44 and 46 are also included in the spirit of the present invention. Preferably, the ports 44, 46 and assemblies 48, 50 are positioned close to the bore 34 in order to minimize torque on the assembly 12 due to the weight of tube assemblies 16 and 18. For example, locating the ports 44, 46 or assemblies 48, 50 at end 58 of the handle 54 would not be preferred because the length of the handle 54 would cause the tubing assemblies 16 and 18 to apply greater leverage on the assembly 12, making it more difficult to control the position of the probe 26. The tube assemblies 16, 18, and 22 make connection to the various parts 14, 20, 48 and 50 by way of connectors 52. The preferred type of connector 52 is known as a Leur connector. Other types of connectors or connections known in the art are also included. A light weight, preferably hollow, handle 54 is shown connected to the housing 28 by way of bolts 56. Other constructions of the handle 54 and interconnection to the housing 28 are also included in the spirit of the present invention, but the preferred embodiment is a light weight handle to minimize torque on the assembly 12. Referring again to the probe assembly 12, although the bore 34 and port 36 of assembly 12 are shown as singular, either or both can be multiple. This is illustrated in FIG. 2, which is an end view of a probe assembly 37 shown in side view in FIG. 3. FIG. 2 shows two smaller bores 72 and 74, and a larger bore 76. FIG. 3 shows sealed ports 78 and 80 at the proximal end of bores 72 and 76 respectively. A similar sealed port is provided at the proximal end of bore 74, but not shown in FIG. 3. These ports are preferably bicuspid valves, providing access for insertion of tools through bores 72, 74 and 76. An irrigation port 82 is shown feeding bore 72, and an evacuation port 84 operating through bore 74. The arrangements shown in FIGS. 1, 2 and 3 are given by way of example. The invention includes provision for one or more tools through one bore, as well as the use of multiple bores for inserting tools and irrigation and evacuation.

Referring again to FIG. 1, the irrigation pump 14 includes an inexpensive, replaceable pump cartridge 62, attached to a motor drive unit 60 by connector assembly 64. The pump cartridge is empowered by the drive unit 60 through connector assembly 64, and this will be fully explained in the following text relating to the figures of the drawing.

The details of the irrigation pump are more fully described in reference to FIGS. 4A and 4B. The cartridge 62 is shown in a cross-sectional view. The cartridge housing 86 is preferably constructed by injection molding to minimize costs. It has a pump cavity 88, connected to inlet line 90 and an exhaust line 92. Leur connectors 94 and 96 are shown on the inlet 98 and exhaust 100 respectively, with corresponding one way valves 102 and 104. The Leur connectors installed in taps 106 and 108 in the housing 86, and ball and spring one way valves, are shown for illustration of the preferred embodiment. Other types of connectors and one way valves are included in the spirit of the invention.

Figure 5B:
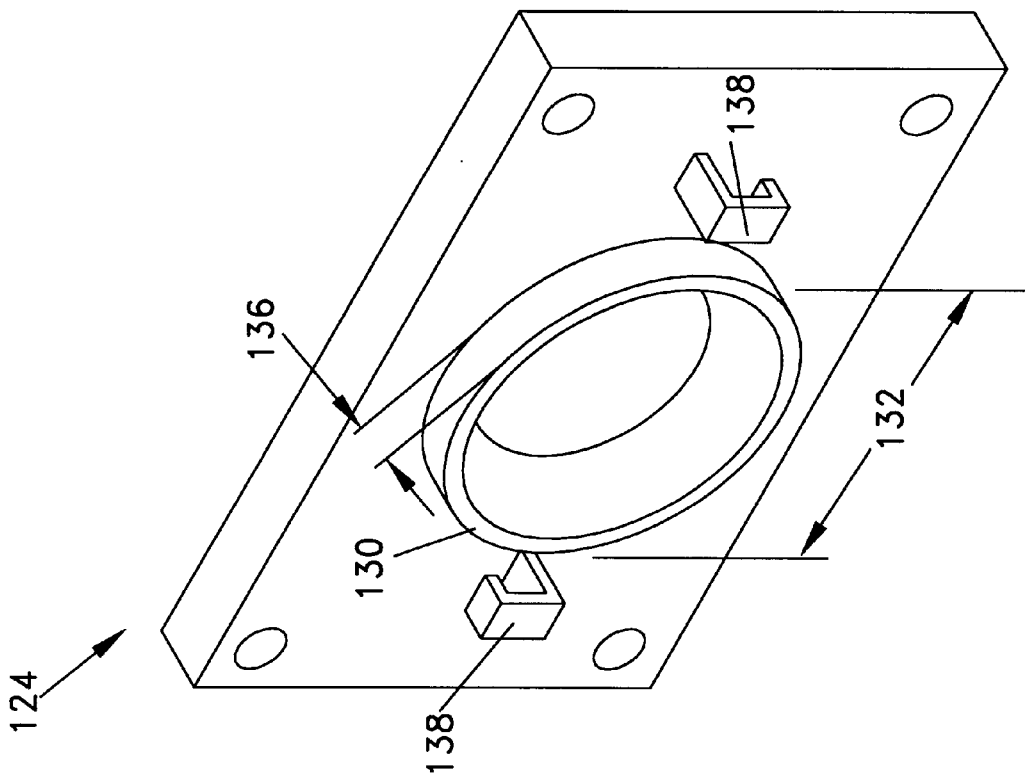
FIG. 5B illustrates a plug for connecting the pump cartridge to the motor drive unit.
Figure 5A:
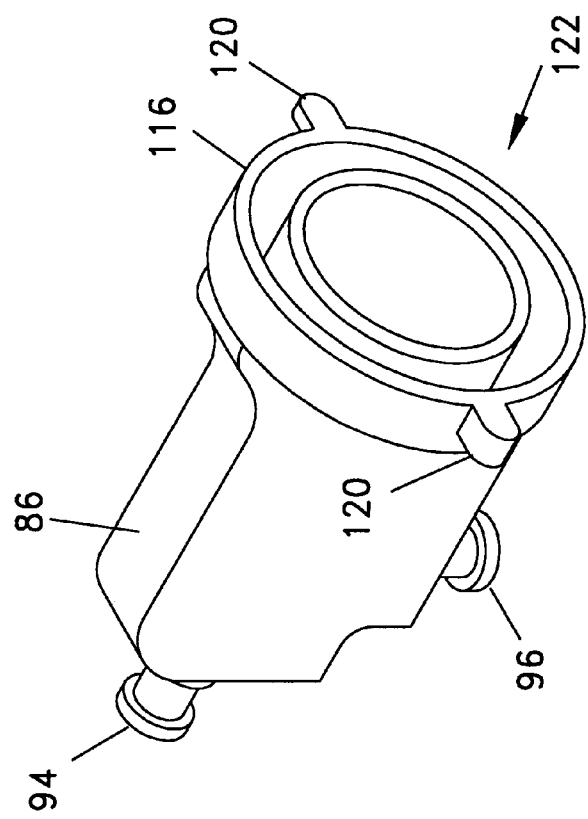
FIG. 5A is a perspective view of the pump cartridge.

A flexible, resilient diaphragm 110 with a circumferential rim 112 is installed with the rim 112 inserted in an annular groove 114. The diaphragm 110 is set in from surface 116 of housing 86. Referring momentarily to FIG. 5A, it can be seen that the surface 116 is annular in shape, and together with the diaphragm 110 forms a shallow cylindrical cavity 118 (FIG. 4A) which combined with tabs 120 forms a connector receptacle 122 for mating with a corresponding connector plug 124 (FIGS. 4B and 5B). The plug 124 is shown attached to pump housing 126 with bolts 128. It has a protruding annular shaped ridge 130 with an outer diameter 132 (FIG. 5B) sized to fit the diameter 134 (FIG. 4A) of cavity 118. The height 136 (FIG. 4B) of the ridge is designed so as to bear on and slightly compress the diaphragm (110) to secure the diaphragm in position and to provide a resilient pressure to maintain mating contact between the receptacle 122 and plug 124. Upon inserting the ridge 130 in the cavity 118, the receptacle is locked with the plug 124 by rotating the housing 86 so as to engage the tabs 120 with resilient clips 138. The engagement position is indicated by the dashed lines 140 in FIG. 4B, showing the housing 86, the cavity 88 and the diaphragm 110. The pumping action is achieved by depressing the diaphragm 110 into the cavity 88 as shown by dashed lines 142 in FIG. 4B to drive fluid out port 100. The action of the diaphragm 110 returning to its normal state creates a vacuum in the cavity 88 which pulls liquid into the cavity from port 98. The diaphragm 110 is depressed by a diaphragm compressor 144 (FIG. 4B), including a diaphragm actuator 146, a sleeve 148, and a crank 150. The crank 150 is turned by drive shaft 152 empowered by motor 154. The actuator 146 has a piston 156 providing a convex drive surface for contact with and depression of the diaphragm 110. The piston as shown is preferably a ball, guided by a bore 158 in the sleeve 148. The piston 156 is joined to a rod 160, which is rotatably connected to a drive pin 162 connected to the crank 150 to the motor drive shaft 152, the crank supplying transformation of the rotation of shaft 152 to reciprocating motion of the rod and piston. The operation of the piston, rod and drive shaft is similar to that in a conventional internal combustion engine, except that in this case, the piston is being driven by the shaft, rather than the shaft by the piston. The ball shape of the piston is a preferred embodiment. It does not require a flex joint between the ball (piston) and the rod. Other designs, however, are also included in the spirit of the present invention, for example, such as a cylindrical piston with a convex surface facing the diaphragm, and a flex joint to the rod.

The speed of the motor 154, and thereby the speed of reciprocation of the piston and resulting flow of fluid is determined by the control 164. An on-off switch 166 is shown for turning on or off energy from a supply bus 168. Other mechanical and electrical details of the structure of the diaphragm compressor system are not required in this description, as such details will be readily understood by those skilled in the art after reading the description of the present invention.

Referring now to FIGS. 6A, 6B and 6C, an embodiment of the probe assembly of the present invention is illustrated wherein bore 168 of three bores 168, 170 and 172 (FIG. 6B) is used to insert a novel electro-surgical apparatus 174. An opening 176 is provided in the side of bore 168 in order for a conductive plate 178, attached at the distal end of the apparatus 174, to make contact or close proximity with tissue 180. The opening 176 as shown is an example of a preferred embodiment. Other opening shapes are also included in the present invention. For example, a complete open area extending to the end 182 of probe 184 is an alternate configuration facilitating contact with the tissue. The electro surgical apparatus 174 includes a probe 186 with an outer elongated cylindrical shaped insulator 188 having a bore 190 therethrough. The insulator 188 has a reduced diameter section 192 on which is attached or deposited one or more of the conductive plates 178, each insulated from the other, and positioned around the circumference of the cylindrical insulator 188. This is more clearly illustrated in FIG. 6C, showing the portion 192 with four plates 178 attached. Also, FIG. 6C shows conductive lines 194 electrically interconnecting plates 178 to a center conductor 196.

Referring again to FIG. 6A, the center conductor 196 is shown to extend from the distal end 198 to point 200, where the conductor is attached to an adaptor 206, preferably constructed of insulative material, and having a connective portion 204 for attachment to a drive 206 of a motor 208. Electrical line 210 for supplying power to the motor is shown leading into the handle 212, controlled by an on-off switch 214. Alternatively, power to the motor 208 can be controlled by a foot switch 216, which can either be an on-off switch or a variable voltage control for varying the speed of the motor 208.

Electrical energy is supplied to the conductor 196, and thereby to the plate(s) 178, through a connector 218 having a contact 220, held against the conductor 196 by spring 222, which makes contact with a connector pin 224 to a banana plug connector 226. Insulative material 228 is provided to insulate the electrically conductive parts (220, 222, 224, 226) from the connector casing 230. Other apparatus for making electrical contact to the plates, including variations in the type of connector 218 and the conductor 196, will be apparent to those skilled in the art, and these are included in the spirit of the present invention.

The function of the plate or plates 178 is to apply electrical energy to tissue 180 for ablation and/or coagulation. Experiment has shown that if a plate 178 is allowed to remain in contact with tissue for a relatively long time, the tissue burns and a cavity is formed. The purpose of the motor 208 and rotating apparatus 174 is to move the plate or plates 178 in and out of contact with tissue 180. The length of time a plate 178 is in contact with tissue 180 can be controlled by the speed of the motor 208. By adjusting the motor speed, the effect on the tissue can be varied from degrees of ablation to coagulation. The energy applied to the plate 178 is generally in the RF frequency range, and it passes from the plate or plates 178 into the tissue 218, most intensely in the tissue area in or near contact with the plate 178, and diminishing as it travels toward an electrical return, in this case normally a conductive plate 232 in contact with a portion of a patient's body exterior in closest proximity to the probe.

The flow of RF energy from the plate(s) 178 is indicated by arrows 234, the energy passing through and being absorbed by the tissue 180, and a remainder collected by return plate/conductor 232 which is connected to an RF power supply return, or passive side. The interconnection is indicated by line 236. The active side of the RF supply is connected to the plug 226. The plate 232 is shown by way of illustration. As above discussed, it usually will be a return plate attached to a patient's body exterior, but plate/conductor 232 can also be in the form of a second probe inserted adjacent to probe 184. The disadvantage of this is the need for a second puncture in the body. The advantage is localization of the RF energy. In some cases, where only small areas of coagulation or ablation are to be treated, the probe 184 can serve as a return path for the RF energy. In this case, the RF will be concentrated near the surface of the tissue 180, indicated by dashed line 238. Other return path designs are included in the spirit of the present invention, as will be apparent to those skilled in the art.

Although the present invention has been described above in terms of a specific embodiment, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. A surgical instrument comprising:
   (a) a probe assembly including
      (i) an elongated probe for insertion into a patient's body interior, said probe having at least one bore therethrough;
      (ii) irrigation means providing passage of fluids for irrigating said body interior; and
      (iii) evacuation means providing passage for evacuating matter from said body interior;
   (b) a pump remotely located from said probe assembly for pumping irrigation fluid from a source of said fluid through said irrigation means into said body interior, said pump including
      (i) a replaceable pump cartridge assembly including
         (a) a cartridge housing assembly having
            (i) a cavity with an opening with a perimeter defined by a first annular rim;
            (ii) a one way fluid inlet to said cavity;
            (iii) a one way fluid outlet from said cavity;
            (iv) a second annular rim surrounding said first annular rim forming an annular channel therebetween;
            (v) at least two tabs extending from said second annular rim and;
            (vi) a flexible diaphragm for covering said opening, said diaphragm having a protruding rim portion for seating in said channel;

(ii) a motor drive assembly including
   (a) a motor drive housing;
   (b) a motor and reciprocating drive for actuating a piston to drive said diaphragm; and
(iii) a plug including
   (a) a flange for attachment to said motor drive housing;
   (b) an annular hole through said flange for passage of said pistson;
   (c) an annular ridge surrounding said hole; and
   (d) at least two clips for securely engaoing said tabs to engage said pump cartridge assembly with said plug and causing said diaphragm to be compressed between said annular ridge and said first annular rim.

2. A surgical instrument as recited in claim 1 further comprising
   tubing assembly means for interconnecting said pump cartridge and said irrigation means.

3. A surgical instrument as recited in claim 1 further comprising
   handle means for use by an operator in positioning said probe assembly.

4. A surgical instrument as recited in claim 1 wherein said bore is sealed at a proximal end of said probe assembly by a sealed port for sealable passage of a surgical tool into said bore.

5. A surgical instrument as recited in claim 4 wherein said sealed port has a bicuspid valve.

6. A surgical instrument as recited in claim 1 wherein said reciprocating drive includes
   (a) a diaphragm actuator including said piston connected to a rod, said piston having a convex surface for compressing said diaphragm;
   (b) a sleeve for guiding said piston;
   (c) a crank for transforming rotational movement of said motor to reciprocating motion of said piston.

7. A surgical instrument as recited in claim 6 wherein said piston is of a ball shape, rigidly attached to said rod.

8. A surgical instrument comprising:
   (a) a probe assembly including
      (i) an elongated probe for insertion into a patient's body interior, said probe having at least one bore therethrough;
      (ii) irrigation means providing passage of fluids for irrigating said body interior; and
      (iii) evacuation means providing passage for evacuating matter from said body interior;
   (b) a pump remotely located from said probe assembly for pumping irrigation fluid from a source of said fluid through said irrigation means into said body interior said pump means including
      (i) a replaceable pump cartridge; and
      (ii) a motor drive unit for empowering said pump cartridge;
   (c) electro surgical apparatus including
      (i) a rotatable probe inserted into and electrically insulated from one of said bores, said rotatable probe having at least one conductive plate attached;
      (ii) motor means having means for attachment to and for rotating said rotatable probe;
      (iii) center conductor means providing an electrically conductive path for conducting RF energy to said at least one conductive plate;
   (d) an opening in said one of said bores positioned for said conductive plate to pass over as said probe is rotated; and
   (e) connector means for conducting RF energy from an RF generator to said electrically conductive path.

* * * * *